United States Patent
Radhakrishnan et al.

(10) Patent No.: US 10,456,562 B2
(45) Date of Patent: Oct. 29, 2019

(54) BRONCHIAL SEALANT DELIVERY METHODS AND SYSTEMS

(71) Applicant: PulmonX Corporation, Redwood City, CA (US)

(72) Inventors: Sri Radhakrishnan, Cupertino, CA (US); Ryan Olivera, Granite Bay, CA (US)

(73) Assignee: Pulmonx Corporation, Redwood City, CA (US)

( * ) Notice: Subject to any disclaimer, the term of this patent is extended or adjusted under 35 U.S.C. 154(b) by 512 days.

(21) Appl. No.: 15/001,598

(22) Filed: Jan. 20, 2016

(65) Prior Publication Data

US 2016/0206301 A1   Jul. 21, 2016

Related U.S. Application Data

(60) Provisional application No. 62/105,649, filed on Jan. 20, 2015.

(51) Int. Cl.
*A61M 25/10* (2013.01)
*A61M 16/04* (2006.01)
(Continued)

(52) U.S. Cl.
CPC ....... *A61M 25/10* (2013.01); *A61B 17/12104* (2013.01); *A61B 17/12186* (2013.01); *A61M 16/04* (2013.01); *A61M 16/0404* (2014.02); *A61M 16/0459* (2014.02); *A61M 16/0479* (2014.02); *A61M 16/0486* (2014.02); *A61M 16/0434* (2013.01); *A61M 2016/0027* (2013.01);
(Continued)

(58) Field of Classification Search
CPC ....... A61B 17/12104; A61B 17/12186; A61M 16/04–16/0497; A61M 25/10; A61M 2025/1052; A61M 2205/3334; A61M 2205/3344

See application file for complete search history.

(56) References Cited

U.S. PATENT DOCUMENTS

7,819,908 B2   10/2010   Ingenito
8,137,302 B2    3/2012   Aljuri et al.
(Continued)

OTHER PUBLICATIONS

Definition of "time". Cambridge Dictionary. Accessed Feb. 11, 2019. <https://dictionary.cambridge.org/dictionary/english/time> (Year: 2019).*

(Continued)

*Primary Examiner* — Kami A Bosworth
(74) *Attorney, Agent, or Firm* — Wilson Sonsini Goodrich & Rosati

(57) ABSTRACT

Devices, methods, and systems are provided for sealing a lung region. The target lung compartment is accessed and isolated via an isolation catheter. Fluid is delivered into the target lung compartment such that the target compartment is pressurized and the fluid flows through the collateral flow channel. A sealing agent is injected into the isolated lung compartment such that the agent is carried by the fluid to the collateral flow channel, thereby sealing the collateral flow channel. Variables of air flow may be measured or analyzed prior to injection of the sealing agent, or the sealing agent may be introduced into the region after a suitable time has elapsed.

11 Claims, 9 Drawing Sheets

(51) Int. Cl.
　　　*A61B 17/12*　　　(2006.01)
　　　*A61M 16/00*　　　(2006.01)
(52) U.S. Cl.
　　　CPC ............... *A61M 2025/1052* (2013.01); *A61M 2202/025* (2013.01); *A61M 2202/0208* (2013.01); *A61M 2205/3334* (2013.01); *A61M 2205/3344* (2013.01); *A61M 2205/505* (2013.01)

(56) References Cited

U.S. PATENT DOCUMENTS

| | | |
|---|---|---|
| 8,445,589 B2 | 5/2013 | Ingenito et al. |
| 2003/0051733 A1 | 3/2003 | Kotmel et al. |
| 2005/0288684 A1* | 12/2005 | Aronson .......... A61B 17/12104 606/108 |
| 2006/0264772 A1 | 11/2006 | Aljuri et al. |
| 2011/0220104 A1 | 9/2011 | Wondka et al. |
| 2012/0149995 A1 | 6/2012 | Mantri et al. |
| 2013/0178426 A1* | 7/2013 | Anzai .................. A61M 16/04 514/17.2 |

OTHER PUBLICATIONS

International search report and written opinion dated Apr. 1, 2016 for PCT/US2016/014183.
"EESR for EP16740705 dated Jul. 20, 2018".

* cited by examiner

BRONCHIAL SEALANT DELIVERY METHODS AND SYSTEMS

CROSS-REFERENCE TO RELATED APPLICATIONS

This application claims priority to U.S. Provisional Patent Application No. 62/105,649 filed on Jan. 20, 2015, the entire content of which is incorporated herein by reference.

FIELD OF THE INVENTION

Present disclosure relates generally to devices, methods, and systems for delivering an agent to a lung region.

BACKGROUND OF THE INVENTION

Pulmonary diseases, such as chronic obstructive pulmonary disease, (COPD), reduce the ability of one or both lungs to fully expel air during the exhalation phase of the breathing cycle. Such diseases are accompanied by chronic or recurrent obstruction to air flow within the lung. Because of the increase in environmental pollutants, cigarette smoking, and other noxious exposures, the incidence of COPD has increased dramatically in the last few decades and now ranks as a major cause of activity-restricting or bed-confining disability in the United States. COPD can include such disorders as chronic bronchitis, bronchiectasis, asthma, and emphysema.

It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue. Consequently, the diseased lung tissue exerts a relatively low driving force, which results in the diseased lung expelling less air volume than a healthy lung. The reduced air volume exerts less force on the airway, which allows the airway to close before all air has been expelled, another factor that prevents full exhalation.

The problem is further compounded by the diseased, less elastic tissue that surrounds the very narrow airways that lead to the alveoli, which are the air sacs where oxygen-carbon dioxide exchange occurs. The diseased tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange.

In addition, hyper-expanded, diseased lung tissue occupies more of the pleural space than healthy lung tissue. In most cases, a portion of the lung is diseased while the remaining part is relatively healthy and, therefore, still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Some recent treatments include the use of devices that isolate a diseased region of the lung in order to reduce the volume of the diseased region, such as by collapsing the diseased lung region. According to such treatments, a delivery catheter is used to implant one or more implantable devices in airways feeding a diseased region of the lung to regulate fluid flow to the diseased lung region in order to fluidly isolate the region of the lung. These implantable devices can be, for example, one-way valves that allow flow in the exhalation direction only, occluders or plugs that prevent flow in either direction, or two-way valves that control flow in both directions.

In addition to the above, it is sometimes desirable to provide methods for sealing collateral flow channels between adjacent lung segments. Such sealing methods may be particularly useful for treating patients prior to endobronchial or other lung volume reduction procedures. Thus, methods and apparatus for sealing collateral flow channels should be compatible with known protocols for occluding diseased lung segments and regions for performing lung volume reduction, including the placement of plugs and occluding members within the airways leading to such diseased lung segments and regions. One such sealing method and system has been described in U.S. Pat. No. 8,137,302. In other cases, sealing agents may be provided, though they are not equipped with the systems or methods for delivery for collateral channels. Other such sealing agents have been used in U.S. Pat. Nos. 7,819,908 and 8,445,589. The objective thus remains to provide additional methods for sealing collateral channels. At least some of these objectives will be met by the disclosures described herein below.

BRIEF SUMMARY OF THE INVENTION

The present disclosure relates to aspects of methods, and systems for occluding a collateral flow channel. In one aspect, a method for occluding a collateral flow channel between a target lung compartment and an adjacent lung compartment is disclosed. Said method comprises accessing the target lung compartment through an isolation catheter, isolating the target lung compartment, delivering a fluid into the target lung compartment such that the target compartment is pressurized and the fluid flows through the collateral flow channel, and injecting an agent into the isolated lung compartment such that the agent is carried by the fluid to the collateral flow channel, thereby sealing the collateral flow channel. The agent is may be a sealant.

The above method may further comprise measuring pressure within the target lung compartment after the compartment is pressurized and determining that the target lung compartment comprises a collateral flow channel based on a measured drop in pressure. Further, pressure within the target lung compartment may be measured and the timing of the injection of the agent may be based on the measured pressure. Timing the injection of the agent may comprise injecting the agent after the measured pressure drops below a predetermined threshold value. Timing the injection of the agent may comprise waiting a predetermined period of time after measuring a drop in pressure before injecting the agent. The injection of the agent may comprise determining that the collateral channel has been sealed based on the measured pressure and stopping the injection of the agent after the collateral channel has been determined to be sealed.

Alternatively, the method may comprise measuring flow rate within the target lung compartment and timing the injection of the agent based on the measured flow rate. Timing the injection of the agent may comprise injecting the agent after the measured flow reaches a predetermined threshold value. Timing the injection of the agent comprises determining that the collateral channel has been sealed based on the measured flow and stopping the injection of the agent after the collateral channel has been determined to be sealed.

Also disclosed is a system for occluding a collateral flow channel between a target lung compartment and an adjacent lung compartment. This system comprises an isolation catheter configured to access and isolate the lung compartment, a fluid delivery mechanism configured to deliver a fluid into the target lung compartment such that the target compartment is pressurized and the fluid flows through the collateral flow channel, an agent delivery mechanism configured to inject the agent into the isolated lung compartment such that the agent is carried by the fluid to the collateral flow channel, thereby sealing the collateral flow channel and a processor configured to receive input from a sensor associated with the isolation catheter, and time the injection of the agent based on the input. In some aspects, the agent within this system is a sealant. The input received by the processor is a measure of pressure within the target lung compartment and the timing of the injection of the agent is based on the measured pressure. Timing the injection of the agent may comprise injecting the agent after the measured pressure drops below a predetermined threshold value. Timing the injection of the agent may comprise waiting a predetermined period of time after measuring a drop in pressure before injecting the agent. Timing the injection of the agent may comprise determining that the collateral channel has been sealed based on the measured pressure and stopping the injection of the agent after the collateral channel has been determined to be sealed.

In some aspects, the input received by the processor is a measure of flow within the target lung compartment and the timing of the injection of the agent is based on the measured flow. Timing the injection of the agent may comprise injecting the agent after the measured flow reaches a predetermined threshold value. Timing the injection of the agent comprises determining that the collateral channel has been sealed based on the measured flow and stopping the injection of the agent after the collateral channel has been determined to be sealed.

The processor is further configured to receive input from a user regarding the injection of the agent. The system further comprises a display unit to display values obtained from the sensor or display calculations derived from input from the sensor.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

DETAILED DESCRIPTION OF THE INVENTION

Figure 1:
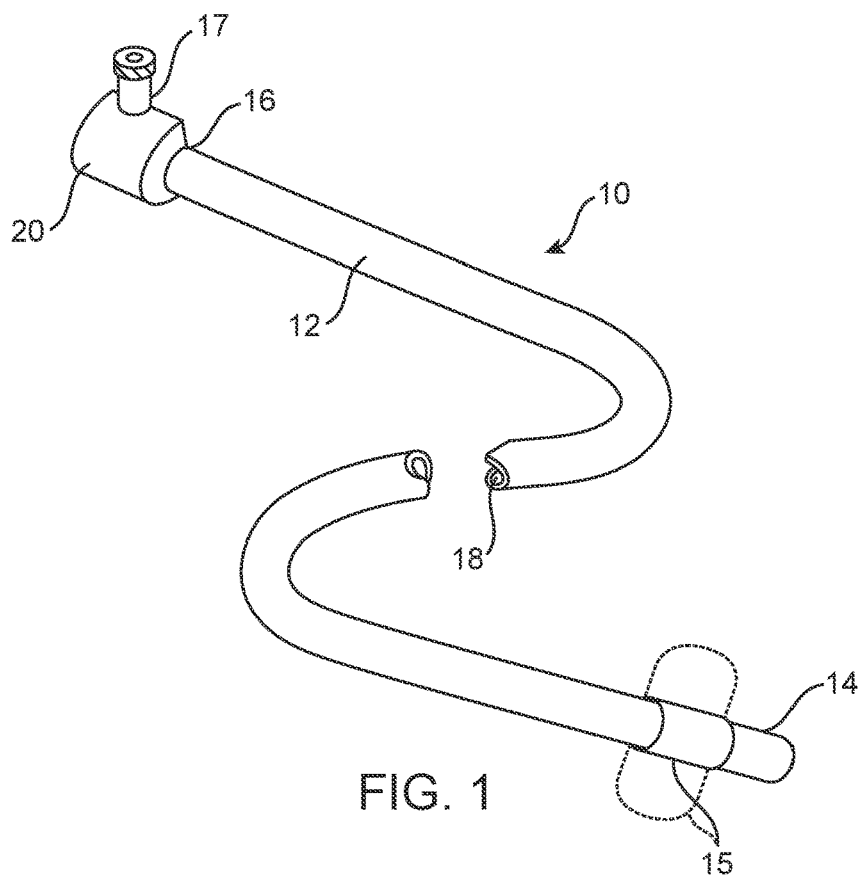
FIG. 1 is a perspective view of one embodiment of an agent delivery catheter.

Although the detailed description contains many specifics, these should not be construed as limiting the scope of the disclosure but merely as illustrating different examples and aspects of the disclosure. It should be appreciated that the scope of the disclosure includes other embodiments not discussed herein. Various other modifications, changes and variations which will be apparent to those skilled in the art may be made in the arrangement, operation and details of the method, device, and system of the present embodiments disclosed herein without departing from the spirit and scope of the disclosure as described here.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Throughout this disclosure, reference is made to the term "agent". As used herein, the term "agent" refers to a sealing agent. For purposes of this application, the term "agent" is interchangeable with "sealant" and "sealing agent."

Throughout this disclosure, reference is made to the term "lung region". As used herein, the term "lung region" refers to a defined division or portion of a lung. For exemplary purposes, lung regions are described herein with reference to human lungs, wherein some exemplary lung regions include lung lobes and lung segments. Thus, the term "lung region" as used herein can refer, for example, to a lung lobe or a lung segment. Such nomenclature conforms to nomenclature for portions of the lungs that are known to those skilled in the art. However, it should be appreciated that the term "lung region" does not necessarily refer to a lung lobe or a lung segment, but can refer to some other defined division or portion of a human or non-human lung.

The present disclosure describes a method for sealing a collateral flow channel between a target lung compartment and an adjacent lung compartment. The method comprises accessing the target lung compartment through an isolation catheter, isolating the target lung compartment; delivering a fluid, such as a gas, into the target lung compartment such that the target compartment is pressurized and the gas flows through the collateral flow channel. Thereafter, an agent, such as a sealant, is injected into the isolated lung compartment such that the agent is carried by the fluid to the collateral flow channel, thereby sealing the collateral flow channel. Optionally, in some aspects, the method comprises measuring pressure within the target lung compartment after the compartment is pressurized. If it is determined that the target lung compartment comprises a collateral flow channel based on a measured drop in pressure, the target lung compartment may be sealed. Optionally, delivery of the agent may be timed based on the measured pressure, to be delivered, for example, when the pressure reaches a predetermined threshold value. Additionally, the method comprises measuring flow within the target lung compartment after the compartment, and delivery of the agent is synchronized with the measured flow reaching a predetermined threshold value. Additionally, systems comprising the application of these methods are also described.

Turning to the figures, FIG. 1 describes a catheter for use in conjunction with the present invention. Similar delivery catheters have been described in U.S. Pat. Nos. 8,137,302 and 7,883,471, which are incorporated herein by reference. Delivery catheter 10 comprises an elongate catheter body 12 having a proximal end 16, and a distal end 14 that comprises an occlusion element 15, which in this case is an inflatable balloon. Catheter body 12 includes at least one central lumen or passage 18 with a distal opening 19 (shown in greater detail in FIGS. 2 and 3). A hub 20 is disposed at the proximal end 16 of the catheter body 12 and includes at least one port 17 for connection to an inflation lumen 21 which feeds an inflation medium to the expandable element 15, for sealing the distal end of the catheter within a lung airway.

Figure 2:
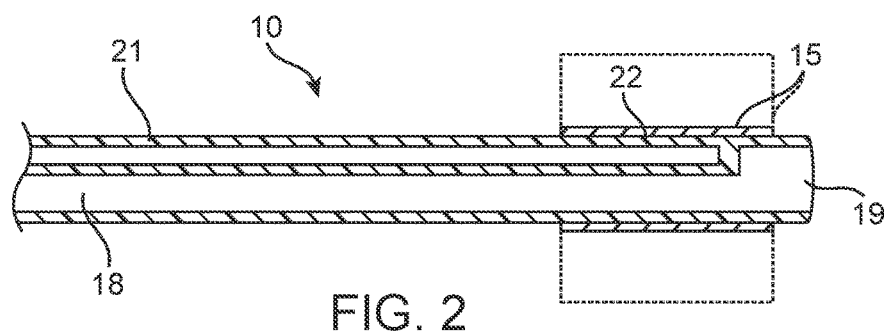
FIG. 2 is an axial, cross-sectional view of a distal portion of one embodiment of an agent delivery catheter comprising a single central lumen for delivery of fluid or agents.
Figure 3:
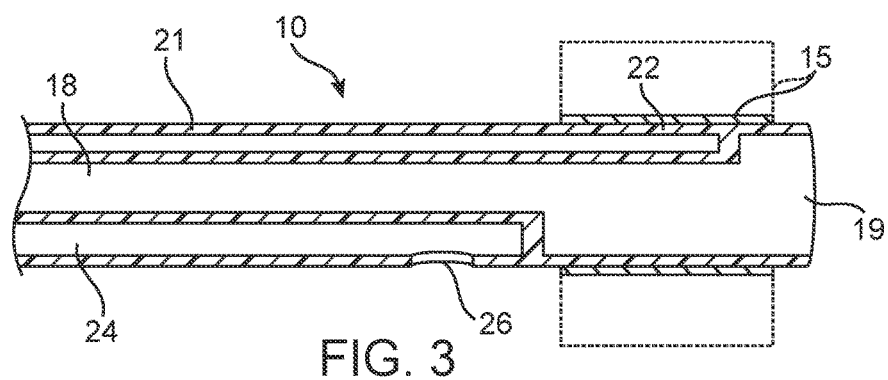
FIG. 3 is an alternative axial, cross-sectional view of the distal region of one embodiment of an agent delivery catheter comprising a central lumen and a second lumen for delivery of an agent.

In the embodiment shown in FIG. 2, catheter 10 comprises a single central lumen or passage 18 for delivery of fluid or agents. The balloon inflation lumen 21 opens through a port 22 to deliver the inflation medium to the expandable member 15. A second embodiment of the catheter 10, as shown in FIG. 3, has the central lumen or passageway 18 and a second lumen or passageway 24 which terminates in at least one side port 26 for delivering the agent, as described in more detail below.

Although not illustrated, catheter 10 may be provided with other features, such as sensors disposed within or in-line with the catheter. Additionally, the catheter may be provided with pull wires or other mechanisms for steering the distal ends of the catheters in order to facilitate advancement through the branching airways of the lung. Still further additionally, the catheters 10 may be provided with optical fibers, small CCD's or other cameras, or other means at their distal ends for visualizing advancement of the catheters through the airways.

The catheter body may be composed of conventional catheter materials to provide the desired flexibility and biocompatibility. Suitable materials include PTFE, PVC, polyurethane, PET, polypropelene or other polymer alloys or interpenetrating network polymers (IPNs) with or without metallic and/or ceramic braid or support. Using such materials, the catheters may be formed by conventional extrusion techniques.

Figure 4:
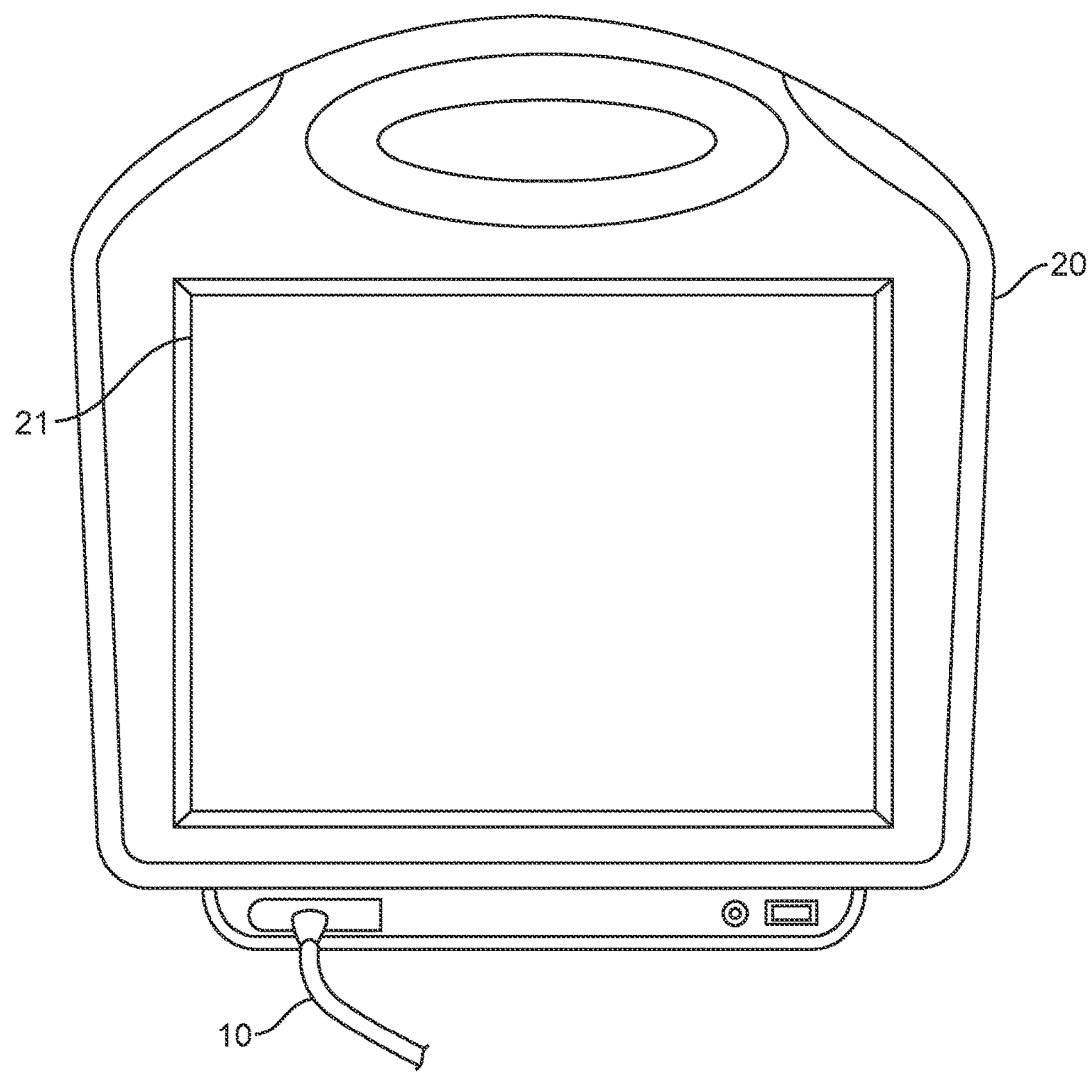
FIG. 4 shows one embodiment of an agent delivery system.

Further, as shown in FIG. 4, the catheter 10 terminates at or is in-line with unit 20 that may include components such as a display unit, a user feedback mechanism and a processor. In this embodiment, the display unit comprises a screen 21 showing input from the one or more sensors within or in-line with the catheter. The user feedback mechanism comprises a mechanism for user input, such as a touchscreen 21. Other user feedback mechanisms may include knobs, dials, buttons, or any other such mechanism. The processor (not shown) is internal or otherwise associated with unit 20 and is configured to perform functions such as receive, process, calculate or relay input from the sensor.

Additionally, the unit 20 may comprise or may be associated with a fluid delivery mechanism (not shown) configured to deliver a fluid (e.g., a gas) via the catheter into the target lung compartment such that the target compartment is pressurized. In some aspects, where collateral channel is present, the fluid may flow through the collateral flow channel. The catheter may also be associated with an agent delivery mechanism (not shown) configured to inject the agent into the isolated lung compartment such that the agent is carried by the fluid to the collateral flow channel, thereby sealing the collateral flow channel. An exemplary agent delivery mechanism maybe a syringe configured to introduce the sealant into the distal end of the catheter such that the sealant moves through the catheter and into the target lung compartment. Such fluid delivery and agent delivery mechanisms may be components held within unit 20, or they may be separate components associated with the unit or the catheter directly.

Further, the processor of the unit is equipped to execute various functions. Such functions may include releasing fluid, releasing an agent, timing the release of the fluid or the agent to a predetermined event or user input, measuring input from a sensor, calculating input from a sensor and relaying input or calculations to a display.

Figure 5A:
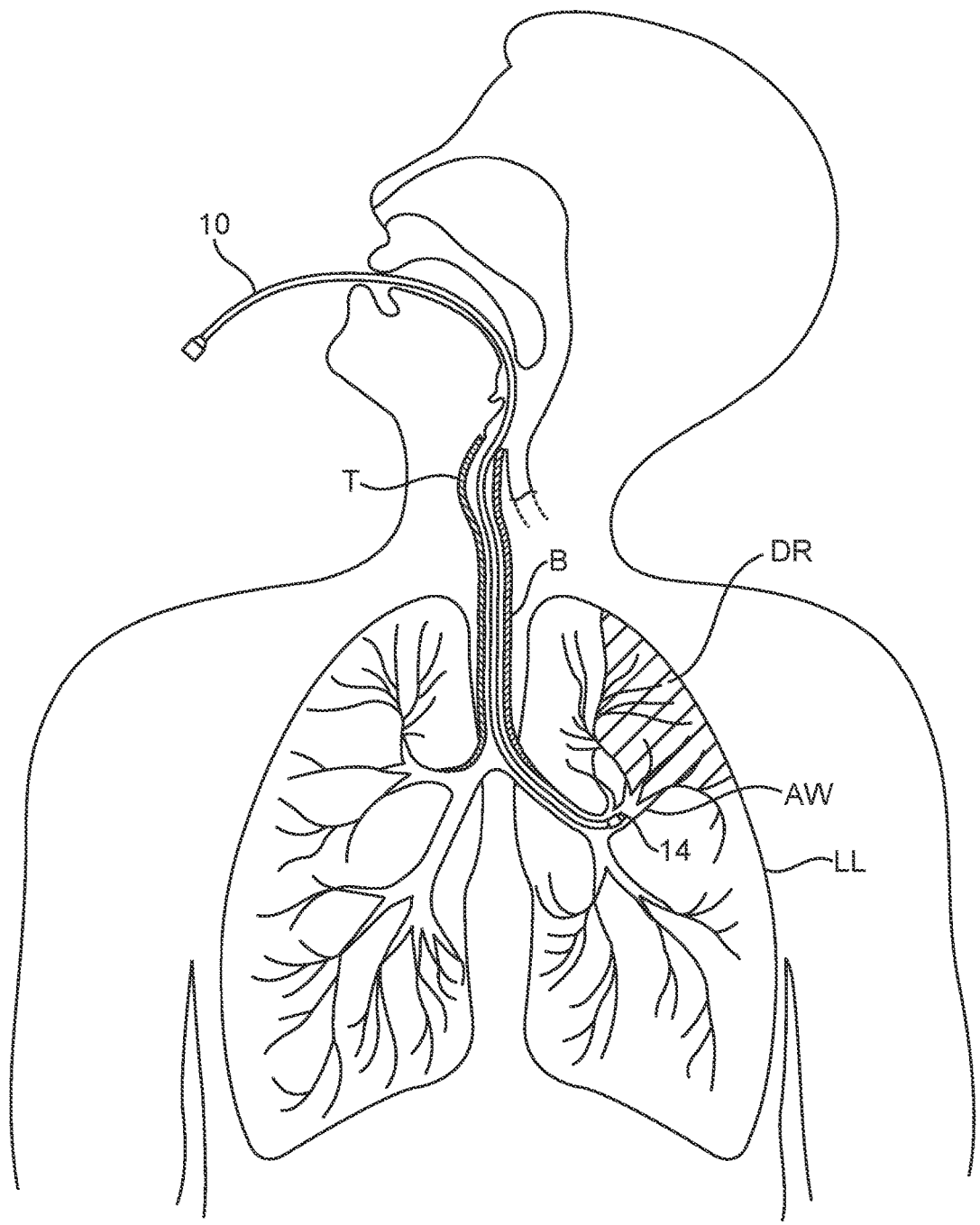
FIGS. 5A-5C illustrate one embodiment of a catheter introduction protocols.

Referring now to FIG. 5A, the respiratory system of the patient starts at the mouth and extends through the vocal cords and into the trachea where it then joins the main stem bronchi B which leads into the lungs, which are comprised of various segments. Each lung segment, also referred to as a bronchopulmonary segment, is an anatomically distinct unit or compartment of the lung which is fed air by a tertiary bronchus and which oxygenates blood through a tertiary artery. Normally, the lung segment and its surrounding fibrous septum (lung walls) are intact units which can be surgically removed or separated from the remainder of the lung without interrupting the function of the surrounding lung segments.

The presence of collateral flow channels in the fibrous septum or wall of a diseased lung segment is problematic since the diseased segment cannot be removed or even isolated successfully with the collateral channels intact. In the case of isolation and deflation of the diseased lung segment, the presence of the collateral channels will permit the reentry of air as the patient breathes. Thus, the present invention, by occluding the collateral passages, returns a perforate or porous lung wall into a functionally intact lung wall which permits subsequent treatment of diseased regions using endobronchial or other treatment protocols.

Use of the agent delivery catheter 10 for treating collateral flow between adjacent lung segments begins with the endotracheal introduction of the catheter 10, as shown generally in FIG. 5A. The catheter 10 is advanced through the mouth, down through the trachea T, and through the main bronchus B into the left lung LL. The distal end 14 of catheter 10 is advanced into the left lung LL, and further advanced via airway AW to a target lung segment DR. The catheter 10 may be introduced through the main bronchus B and into the left lung LL without the use of a bronchoscope or other primary introducing catheter, as exemplarily shown in FIG. 5A.

Figure 5B:
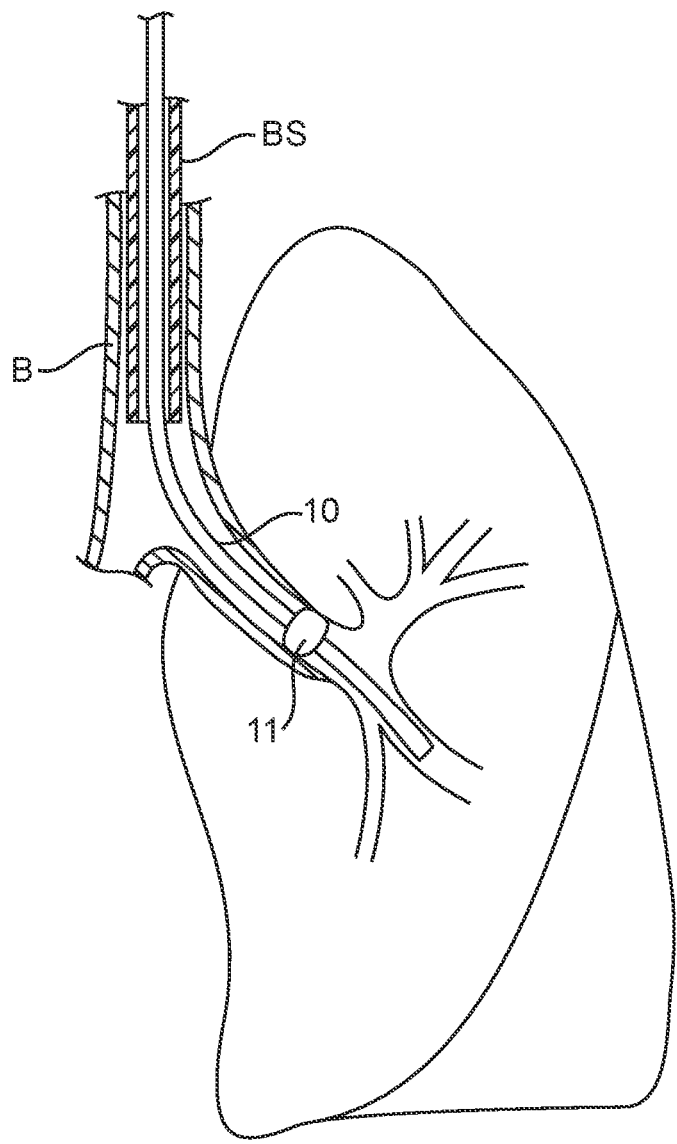
Figure 5C:
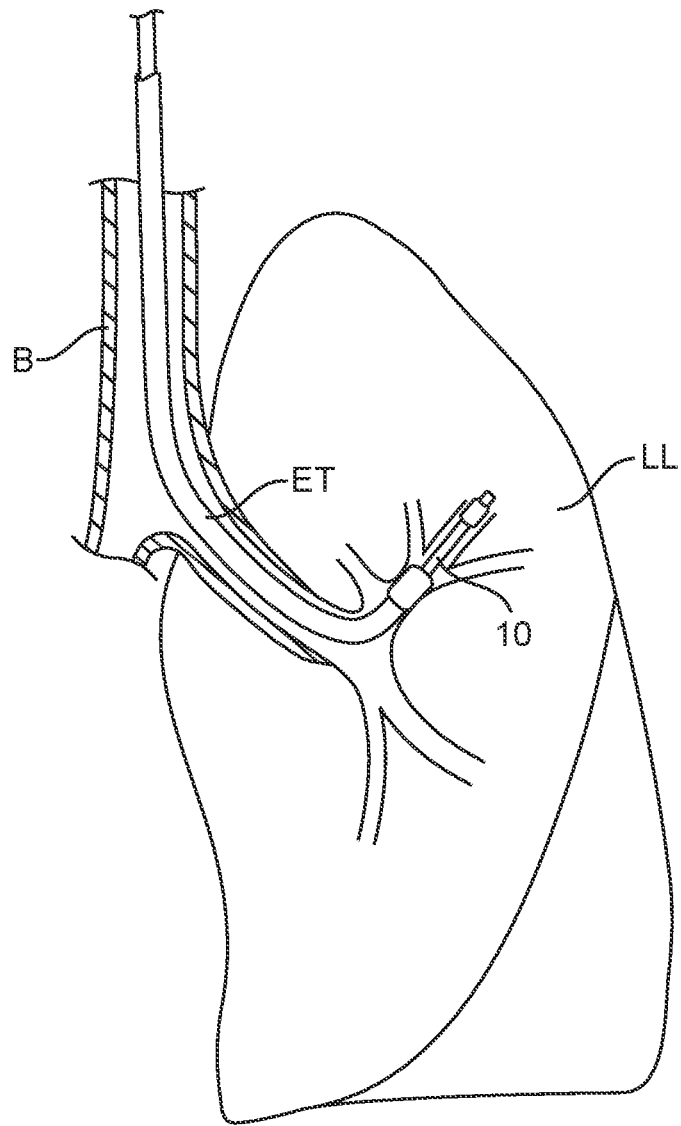

More commonly, as shown in FIG. 5B, catheter 10 may be introduced through a conventional bronchoscope BS. Use of a scope such as a bronchoscope which is capable of advancing into the lung is advantageous in that it facilitates visually-based positioning of the catheter 10 at the desired airway leading to a target lung segment. Alternatively, as shown in FIG. 5C the catheter 10 may be introduced into the lung through any other scope, such as a visualizing endotracheal tube ET or bronchoscope with an inflatable cuff (not shown) which isolates an area of the lungs and permits local control of factors such as lung pressurization.

Optionally, catheter 10 may have an occlusion cuff or balloon 11 near its distal end to anchor the catheter. Construction and use of a visualizing endotracheal tube is taught, for example, in U.S. Pat. No. 5,285,778, the full disclosure of which is incorporated herein by reference. It would be possible, of course, to utilize both the bronchoscope BS and the endotracheal tube in combination for positioning the catheter 10 in the desired lung segment airway.

Figure 6A:
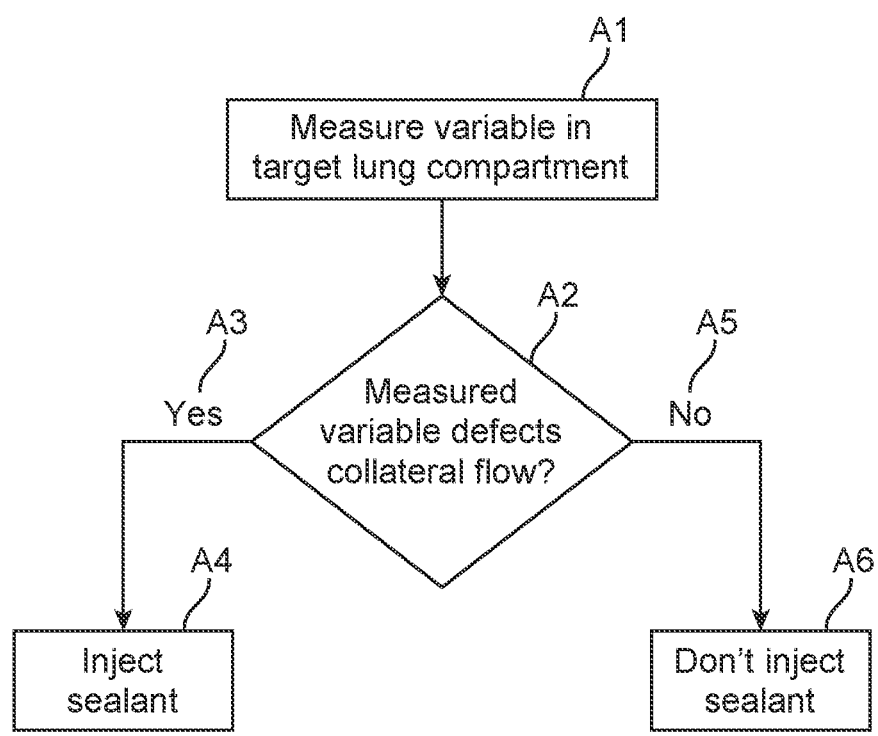
FIGS. 6A, 6B and 6C are flow charts that describe one embodiment of a method of using delivering an agent.
Figure 6B:
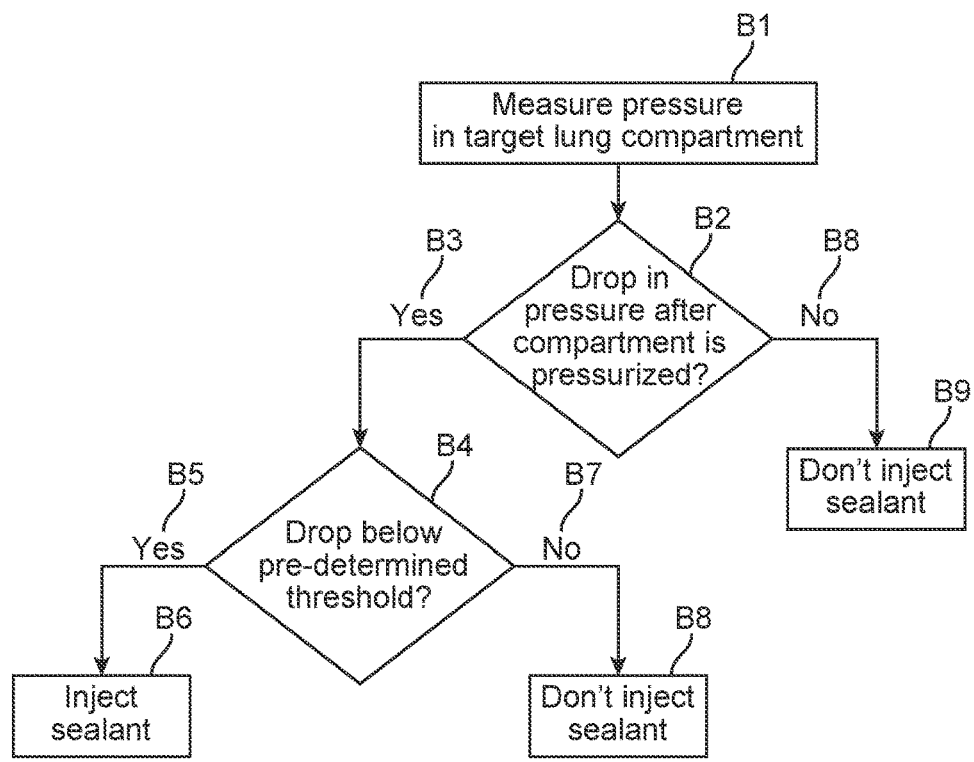
Figure 6C:
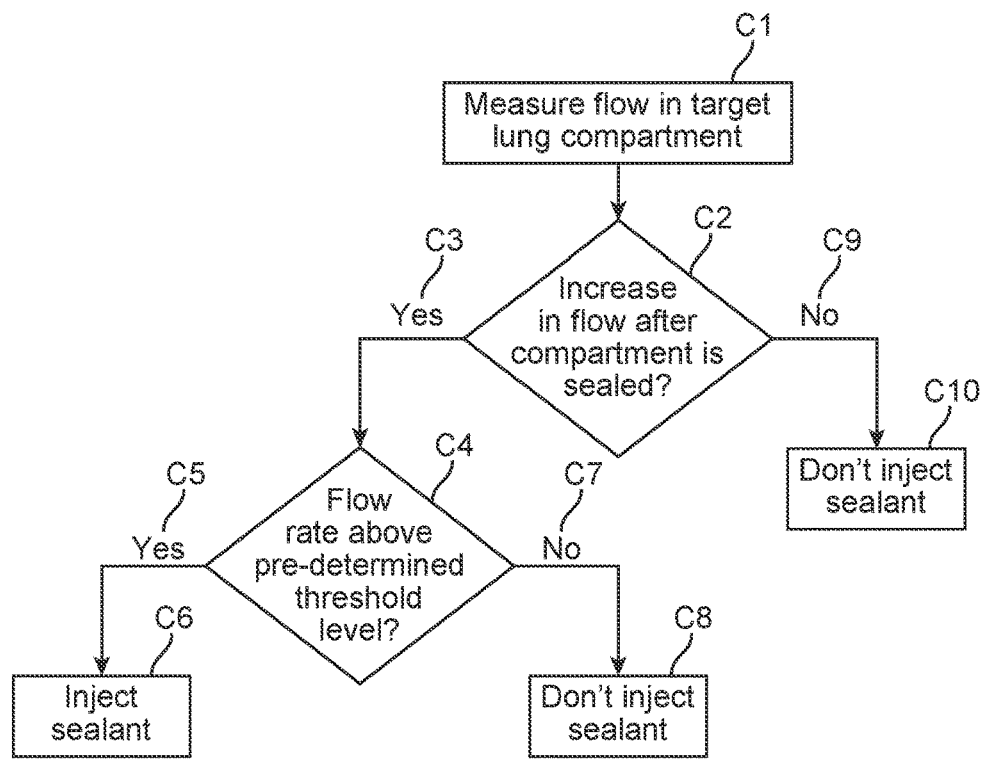
Figure 7A:
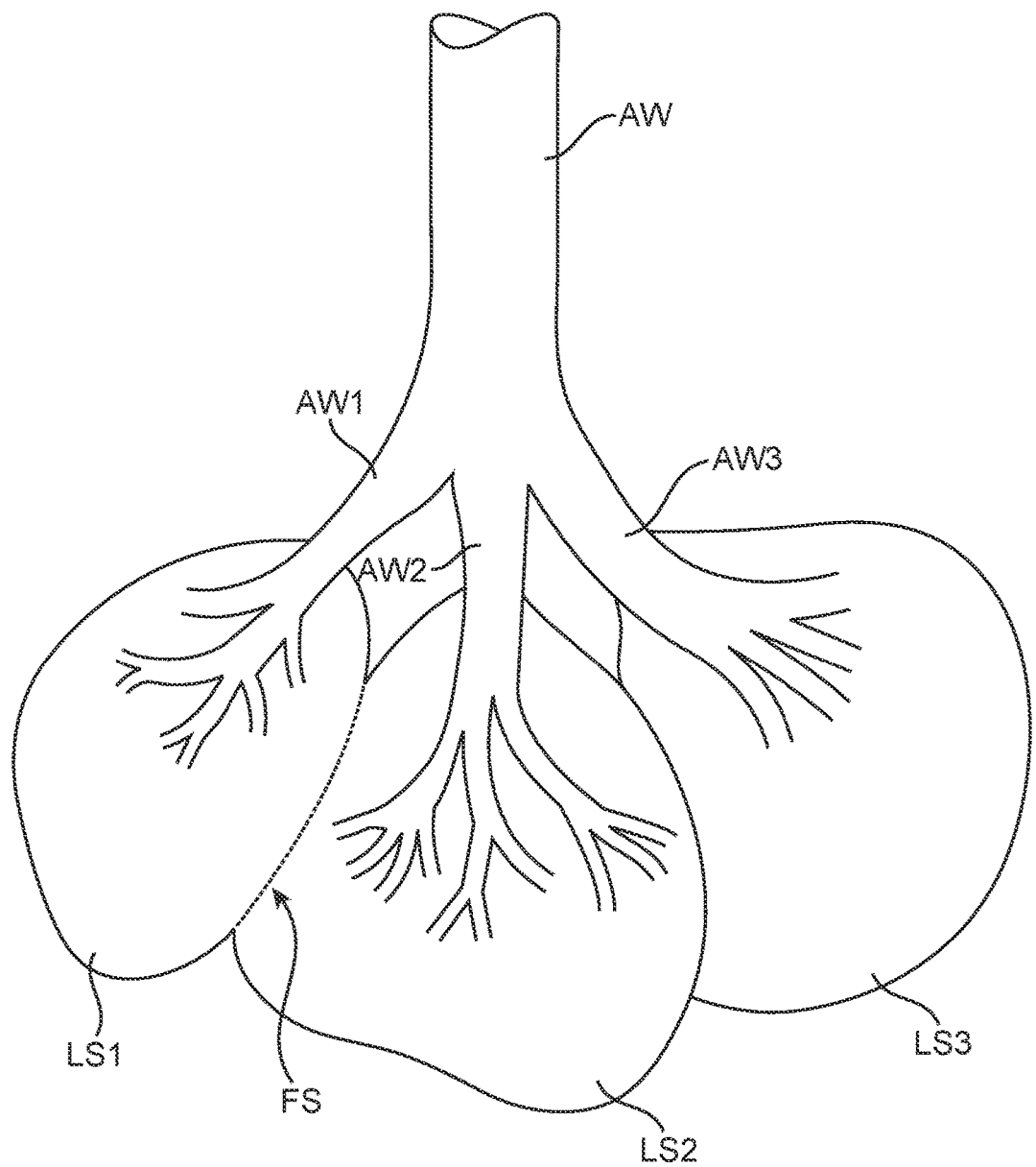
FIGS. 7A and 7B show one exemplary delivery of an agent to collateral flow channels.
Figure 7B:
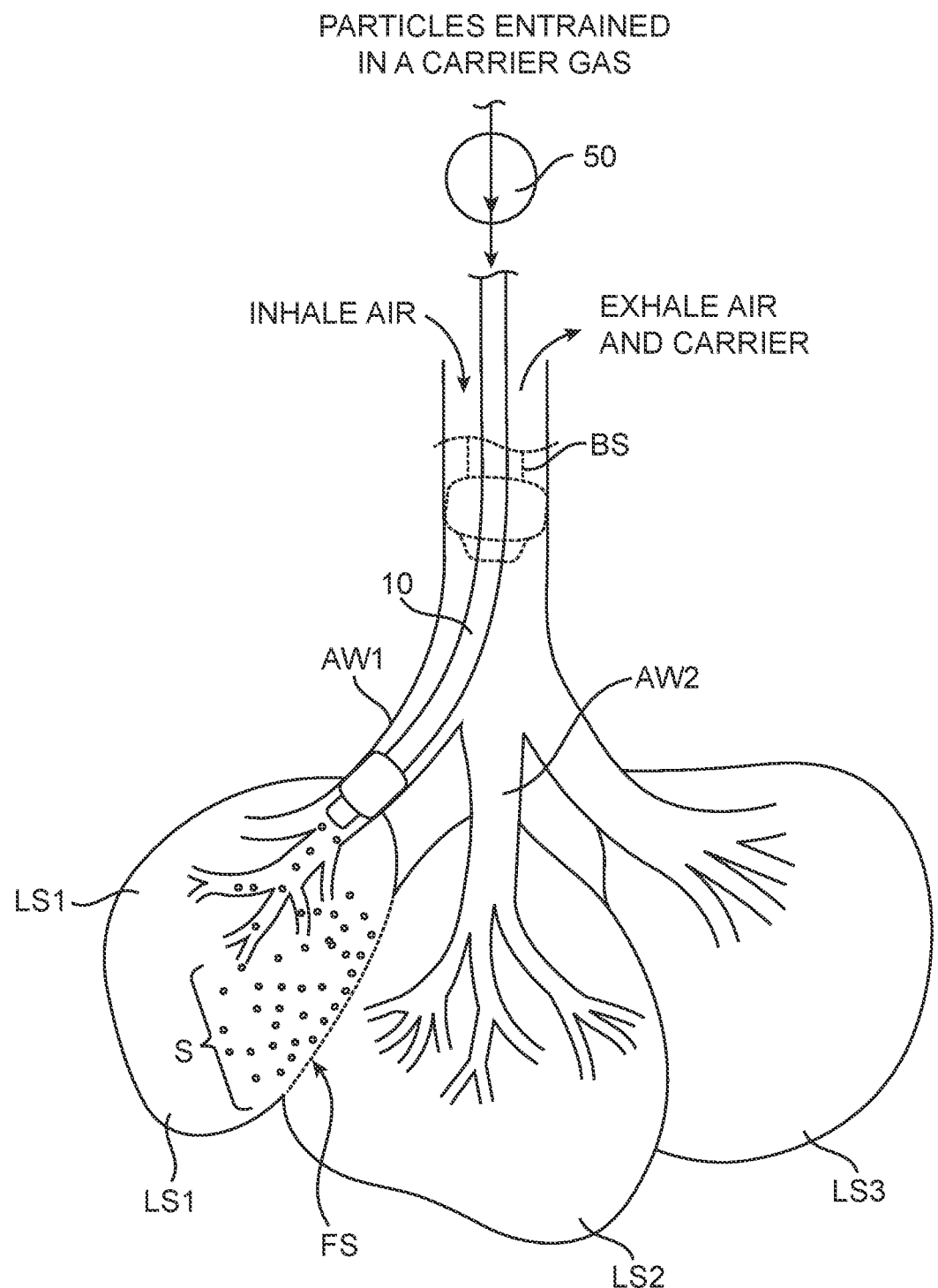

FIGS. 6A, 6B and 6C are flow charts that describe the method of using the above embodiments, while FIGS. 7A and 7B are visual representations of the methods captured in the flow charts. The catheter is placed in a target lung compartment, and one or more variables within the target lung compartment are measured. As described in FIG. 6A, a variable of air flow is measured within the target lung compartment (step A1), and as in step A2, the processor or a user determines whether the measured variable detects collateral flow, such as would occur in the presence of a collateral flow channel. If, as in Step A3, collateral flow is detected, then, as in Step A4, sealant is injected into the target lung compartment to stop collateral flow. If, however, as in Step A5, no collateral flow is detected, then, as in Step A6, the sealant is injected into the target lung compartment. The sealant may be injected directly, or may be injected in conjunction with a carrier, for example a fluid such as a gas.

FIGS. 6B and 6C show how specific variables may be measured and how such measurements may be used to determine when the sealant is injected into the lung compartment. In FIG. 6B, the measured variable is pressure. In an embodiment, the balloon is inflated and the target lung compartment is isolated. The compartment may be pressurized via methods described in U.S. Pub. No. 20030051733, the full disclosure of which is incorporated herein by reference. A fluid may be delivered to the target lung compartment such that the target compartment is pressurized. In Step B1, the pressure of the pressurized lung compartment is measured, and, as shown in B2, it is determined whether there is a drop in pressure. If, as shown in Step B3, the pressure drops, this is an indication of collateral flow to an adjacent channel, since the delivered fluid will flow from the target lung compartment through the collateral flow channels into the adjacent compartment. An agent may then be injected into the lung compartment in order to seal the collateral flow channels. The agent may be selectively directed to the collateral flow channels while little or no agent is delivered to other portions of the target lung compartment. In an embodiment, the agent is injected into the isolated lung compartment such that the agent is carried by the fluid. The fluid flow guides the agent into the collateral flow channel and the pressure in the other areas prevent the agent from going that direction. In various embodiments, the injection of the agent may be timed in order to optimize selective delivery to the collateral flow channels. It is determined as in B4, whether the pressure drops below a threshold level. As shown in B5 and B6, if there is a decrease in pressure that reaches a predetermined threshold, then sealant is injected into the compartment, either alone or in conjunction with a carrier fluid. As shown in B7 and B8, if there is no decrease in pressure, then the sealant is not injected into the target lung compartment. Optionally, the sealant may be injected instantaneously upon measuring a drop in pressure. Additionally, the sealant may be injected after waiting for a period of time at any point after a drop in pressure is detected, and such period of time may be either a preset or predetermined period of time, or it may be a period of time determined by a user. Optionally, a feedback mechanism may exist where it may be determined based on measured pressure that any collateral channels have been sealed. In such an instance, the flow of the sealant is terminated when it is determined that the collateral channels have been sealed.

In FIG. 6C, the measured variable is flow rate. In an embodiment, the balloon is inflated and the target lung compartment is isolated. The compartment may then be pressurized. An agent may be selectively directed to the collateral flow channels while little or no agent is delivered to other portions of the target lung compartment. In an embodiment, the agent is injected into the isolated lung compartment such that the agent is carried by the fluid. The fluid flow guides the agent into the collateral flow path thereby sealing the collateral flow channel and the pressure in the other areas prevent the agent from going that direction. In various embodiments, the injection of the agent may be timed in order to optimize selective delivery to the collateral flow channels. In Step C1, the flow rate is measured in the target lung compartment, and in C2, the processor or a user determines whether there is an increase in flow rate. If, as in C3, there is an increase in flow rate, it is determined, as in C4, whether the flow rate rises above a threshold level. As shown in C5 and C6, if there is an increase in flow rate that reaches a predetermined threshold, then sealant is injected into the compartment, either alone or in conjunction with a carrier fluid. As shown in C7 and C8, if there is no increase in flow rate, then sealant is not injected into the machine. Optionally, the sealant may be injected instantaneously upon measuring a rise in flow rate. Additionally, the sealant may be injected after waiting for a period of time at any point after a rise in flow rate is detected, and such period of time may be either a preset or predetermined period of time, or it may be a period of time determined by a user. Optionally, a feedback mechanism may exist where it may be determined based on measured flow that any collateral channels have been sealed. In such an instance, the flow rate of the sealant is terminated when it is determined that the collateral channels have been sealed.

Alternatively, the sealant may be injected into the target lung region independent of any feedback relating to a variable within the target lung compartment. In such an instance, the user would wait a predetermined period of time, or for the occurrence of a predetermined sequence of events, prior to introducing the sealant.

In each of the examples given in this disclosure, the sealant may take any form such as a gel, particles, aerosol, liquid, or autologous blood. The sealant may be injected via a carrier fluid, such as a gas introducible into a human lung.

FIGS. 7A and 7B show the practice of the methods described in FIGS. 6A, 6B, 6C. As seen in FIG. 7A, the individual lobes of a lung each comprise a plurality of lung segments LS which are fed by individual branches of the bronchi or airways AW. For example, a first lung segment LS1, a second lung segment LS2, and a third lung segment LS3 may be fed from a single airway AW which divides into three branches AW1, AW2, and AW3, as illustrated in FIG. 7A. In the cases of diseased or other compromised lung segments, however, the fibrous septum may be perforate or porous to provide collateral flow channels therebetween, as illustrated at FS.

Referring now to FIG. 7B, the catheter 10 is positioned in airway AW1 leading into lung segment LS1, which may be a diseased lung segment. The collateral flow channels in the wall FS between the first lung segment LS1 and the second lung segment LS2 will permit gas flow in either direction prior to the treatments of the present invention. By expanding the expandable member 15 in the first airway AW1, the first lung segment LS1 is isolated, and this isolation is compromised only by any collateral flow channels that allow air to leak in from adjacent lung compartments. If there is no collateral flow, then the pressure in the compartment will increase, while the flow will decrease. As discussed above, when the presence of collateral flow is determined, sealant S is released into the target lung compartment. Sealant S will thereafter permeate into and seal collateral channels. The catheter is thereafter retracted (not shown), leaving the lung segment LS1 with fewer or no collateral channels.

While the above is a complete description of various embodiments, any of a number of alternatives, modifications, and equivalents may be used in alternative embodiments. Therefore, the above description should not be taken as limiting the scope of the invention as it is defined by the appended claims.

What is claimed is:

1. A method for occluding a collateral flow channel between a target lung compartment and an adjacent lung compartment, said method comprising:
    accessing the target lung compartment through an isolation catheter;
    isolating the target lung compartment;
    delivering a fluid into the target lung compartment such that the target lung compartment is pressurized and the fluid flows through the collateral flow channel;
    measuring pressure within the target lung compartment after the target lung compartment is pressurized;
    determining that the target lung compartment comprises a collateral flow channel based on a measured drop in pressure; and
    injecting an agent into the isolated target lung compartment such that the agent is carried by the fluid to the collateral flow channel, thereby sealing the collateral flow channel; wherein a start or a stop of the injection of the agent is timed by a processor based on the measured pressure.

2. The method of claim 1, wherein the agent is a sealant.

3. The method of claim 1, wherein the start of the injection of the agent is timed by the processor, wherein timing the start of the injection of the agent comprises starting the injection of the agent after the measured pressure drops below a predetermined threshold value.

4. The method of claim 3, wherein timing the start of the injection of the agent comprises injecting the agent instantaneously upon measuring the drop in pressure.

5. The method of claim 1, wherein the start of the injection of the agent is timed by the processor, wherein timing the start of the injection of the agent comprises waiting a predetermined period of time after measuring the drop in pressure before injecting the agent.

6. The method of claim 1, wherein the stop of the injection of the agent is timed by the processor, wherein timing the stop of the injection of the agent comprises determining that the collateral flow channel has been sealed based on the measured pressure and stopping the injection of the agent after the collateral flow channel has been determined to be sealed.

7. A method for occluding a collateral flow channel between a target lung compartment and an adjacent lung compartment, said method comprising:
    accessing the target lung compartment through an isolation catheter;
    isolating the target lung compartment;
    delivering a fluid into the target lung compartment such that the target lung compartment is pressurized and the fluid flows through the collateral flow channel;
    measuring flow within the target lung compartment; and
    injecting an agent into the isolated target lung compartment such that the agent is carried by the fluid to the collateral flow channel, thereby sealing the collateral flow channel; wherein a start or a stop of the injection of the agent is timed by a processor based on the measured flow.

8. The method of claim 7, wherein the start of the injection of the agent is timed by the processor, wherein timing the start of the injection of the agent comprises starting the injection of the agent after the measured flow reaches a predetermined threshold value.

9. The method of claim 8, wherein timing the start of the injection of the agent comprises injecting the agent instantaneously upon measuring a rise in flow.

10. The method of claim 7, wherein the stop of the injection of the agent is timed by the processor, wherein timing the stop of the injection of the agent comprises determining that the collateral flow channel has been sealed based on the measured flow and stopping the injection of the agent after the collateral flow channel has been determined to be sealed.

11. The method of claim 7, wherein the start of the injection of the agent is timed by the processor, wherein timing the start of the injection of the agent comprises waiting a predetermined period of time after measuring a rise in flow before injecting the agent.

* * * * *